United States Patent [19]
Jaffe et al.

[11] Patent Number: 5,843,181
[45] Date of Patent: *Dec. 1, 1998

[54] BIOLOGICAL MATERIAL PRE-FIXATION TREATMENT

[75] Inventors: Norman Jaffe, Dana Point; Warren D. Hancock, Newport Beach, both of Calif.

[73] Assignee: Hancock Jaffe Laboratories, Irvine, Calif.

[*] Notice: The term of this patent shall not extend beyond the expiration date of Pat. No. 5,595,571.

[21] Appl. No.: 786,395

[22] Filed: Jan. 17, 1997

Related U.S. Application Data

[62] Division of Ser. No. 442,017, May 16, 1995, which is a division of Ser. No. 229,452, Apr. 18, 1994, Pat. No. 5,595,571.

[51] Int. Cl.$^6$ ................................ A61F 2/24; B01C 3/00
[52] U.S. Cl. ................................................ 623/2; 8/94.11
[58] Field of Search ................................ 623/2, 900, 11; 8/94.11

[56] References Cited

U.S. PATENT DOCUMENTS

| | | |
|---|---|---|
| 4,050,893 | 9/1977 | Hancock . |
| 4,083,066 | 4/1978 | Schmitz et al. . |
| 4,120,649 | 10/1978 | Schechter . |
| 4,239,492 | 12/1980 | Holman et al. . |
| 4,323,358 | 4/1982 | Lentz et al. . |
| 4,378,224 | 3/1983 | Nimni et al. . |
| 4,383,832 | 5/1983 | Fraefel et al. . |
| 4,402,697 | 9/1983 | Pollock et al. . |
| 4,405,327 | 9/1983 | Pollock . |
| 4,553,974 | 11/1985 | Dewanjee . |
| 4,647,283 | 3/1987 | Carpentier et al. . |
| 4,648,881 | 3/1987 | Carpentier et al. . |

(List continued on next page.)

FOREIGN PATENT DOCUMENTS

| | | |
|---|---|---|
| 2089336 | 2/1993 | Canada . |
| 0128706 | 12/1984 | European Pat. Off. . |
| 0564786 | 10/1993 | European Pat. Off. . |
| 2523810 | 9/1983 | France . |
| 2715466A1 | 6/1977 | Germany . |
| 2169386 | 7/1986 | United Kingdom . |
| WO84/01894 | 5/1984 | WIPO . |

OTHER PUBLICATIONS

"Damage of Porcine Aortic Valve Tissue Caused by the Surfactant Sodiumdodecylsulphat," Bodnar, et al., *Thorac, Cardiovasc. Surgeon*, vol. 2, pp.. 82–85, 1986.

"Degeneration and Calcification of Bioprosthetic Cardiac Valves," Bioprosthetic Tricuspid Valve Implantation in Sheep, Barnhart, et al., *Animal Model of Human Diseases*, pp. 136–139.

"Techniques for Prevention of Calcification of Valvular Bioprostheses," Carpentier, et al., *Valvular Heart Disease*, vol. 70 (Suppl I), Sep. 1984.

(List continued on next page.)

*Primary Examiner*—David H. Willse
*Attorney, Agent, or Firm*—Knobbe, Martens, Olson & Bear, LLP

[57] ABSTRACT

Disclosed is a controlled autolysis method for making biological tissue substantially acellular by exposing the biological material, prior to any fixation thereof, to at least one buffered solution having a pH in the range from about 5.0 to 8.0 and a temperature in the range from about 12° C. to 30° C. for a sufficient period of time to render at least one region of the biological material substantially acellular while substantially preserving the structural integrity and non-cellular structural components of the biological material. Also disclosed is a method of making a bioprosthetic heart valve using biological material that has been treated by controlled autolysis and a method of treating a mammal having a defective heart valve using a bioprosthetic heart valve made, in part, by controlled autolysis.

32 Claims, 7 Drawing Sheets
(6 of 7 Drawing Sheet(s) Filed in Color)

U.S. PATENT DOCUMENTS

| | | |
|---|---|---|
| 4,704,131 | 11/1987 | Noishiki et al. . |
| 4,729,139 | 3/1988 | Nashef . |
| 4,770,665 | 9/1988 | Nashef . |
| 4,776,853 | 10/1988 | Klement et al. . |
| 4,786,287 | 11/1988 | Nashef et al. . |
| 4,798,611 | 1/1989 | Freeman, Jr. . |
| 4,800,603 | 1/1989 | Jaffe . |
| 4,801,299 | 1/1989 | Brendel et al. ............................. 623/1 |
| 4,838,888 | 6/1989 | Nashef . |
| 4,885,005 | 12/1989 | Nashef et al. . |
| 4,976,733 | 12/1990 | Girardot . |
| 4,996,054 | 2/1991 | Pietsch et al. . |
| 5,002,566 | 3/1991 | Carpentier et al. . |
| 5,094,661 | 3/1992 | Levy et al. . |
| 5,104,405 | 4/1992 | Nimni . |
| 5,145,771 | 9/1992 | Lemasters et al. . |
| 5,192,312 | 3/1993 | Orton . |
| 5,215,541 | 6/1993 | Nashef et al. . |
| 5,336,616 | 8/1994 | Livesay et al. . |
| 5,397,353 | 3/1995 | Oliver et al. .............................. 623/11 |
| 5,595,571 | 1/1997 | Jaffe et al. ............................... 8/94.11 |

OTHER PUBLICATIONS

"Possible Causes for the Calcification of Glutaraldehyde–Treated Tissue Heart Valves and Blkiood Contacting Elastomers During Prolonged Use in Medical Devices: A Physicochemical View," S.D. Bruck, *Biomaterials*, vol. 2, 1981.

"Treatment of Tissues or Ogans (e.g. pig heart valves) Used for Animal or Human Transplant," Glick et al., Derwent Publications Ltd., 1 page, 1988.

"Calcific Deposits in Porcine Bioprostheses: Structure and Pathogenesis," Ferrans et al., *The American Journal of Cardiology*, vol. 46, 1980.

"The Cryopreserved Homograft Valve in the Pulmnary Position: Mid–Term Results and Technical Consideration," Lamberti, et al., *Journal of Cardiac Surgery*, vol. 6, No. 4, Supplement, pp. 627–632, 1991.

"Aortic Valve Allografts for Mitral Valve Replacement," Stinson, et al., *Surgery*, vol. 77, No. 6, pp. 861–867, Jun. 1975.

"Calcification of Glutaraldehyde–Preserved Porcine Xenografts in Young Patients," Curcio et al., *J. Thorac, Cardiovasc. Surgery*, vol. 81, pp. 621–625, 1981.

"Calcification of Glutaraldehyde–Preserved Porcine and Bovin Xenograft valves in Young Children," Fiddler et al., *The Annals of Thoractice Surgery*, vol. 35, No. 3, pp. 257–261, Mar. 1983.

"A Study of the Cells in the Explanted Viable Cryopreserved Allograft Valve," O'Brien et al., *Journal of Cardiac Surgery*, vol. 3, pp. 279–287, Supplement, 1988.

"Calcific Stenosis of the Porcine Heterograft," Lamberti et al., *The Annals of Thoracic Surgery*, vol. 28, No. 1, pp. 28–32, 1979.

"Calification in Porcine Xenograft Valves in Children," Silver et al., *The American Journal of Cardiology*, vol. 45, pp. 685–689, Mar. 1980.

"Calcification of Porcine Prosthetic Heart valves: A Radiographic and Light Microscopic Study," Cipriano et al., *Circulation*, vol. 66, No. 5, pp. 1100–1104, Nov. 1982.

"Marked Thrombosis and Calcification of Porcine Heterograft Valves," Platt et al., *Circulation*, vol. 62, No. 4, pp. 862–869, oct. 1980.

"Durability of the Viable Aortic Allograft," Angell et al., *J. Thorac. Cardiovasc. Surg.*. vol. 98, pp. 48–56, 1989.

BIOLOGICAL MATERIAL PRE-FIXATION TREATMENT

RELATED APPLICATION

This application is a divisional of Application Ser. No. 08/442,017, filed May 16, 1995; which is a divisional of Application Ser. No. 08/229,452, filed Apr. 18, 1994, now U.S. Pat. No. 5,595,571.

FIELD OF THE INVENTION

This invention relates to methods for rendering biological materials substantially acellular and for methods of treating biological materials to inhibit their mineralization after implantation into a human or animal. In one embodiment, this invention relates to a method of inhibiting post-implantation mineralization of a bioprosthetic heart valve.

BACKGROUND OF THE INVENTION

Disorders of the cardiac valves cause significant morbidity and mortality. These disorders affect persons of all ages and can result from congenital or degenerative conditions, as well as from the sequelae of infections. Stenosis and insufficiency of the aortic or mitral valves have a greater incidence than stenosis and insufficiency of the tricuspid and pulmonary valves.

Treatment of cardiac valvular disorders can require replacement of the defective valve with a prosthetic valve. There are two types of prosthetic heart valves. "Mechanical valves", the first type, are composed wholly of materials not derived from living organisms. Mechanical valves currently in use have either a ball-valve construction, a tilting disc construction or a hinged leaflet construction.

"Bioprosthetic valves", the second type of prosthetic heart valves, are composed in whole or in part of biological material. Bioprosthetic valves generally comprise a supporting stent and a plurality of leaflets. The leaflets generally comprise biological material, while the stent, if present, generally comprises non-biological material, at least in part. The biological material of the leaflets, can be of autologous tissues, such as pericardium, fascia lata or cardiac valves. Alternately, this material can be derived from homologous tissue, such as non-autologous human tissue for human implantation, or can be xenogeneic.

Each type of prosthetic heart valve has advantages and disadvantages. Mechanical heart valves are durable but they carry a significant risk of thrombus formation with secondary complications. Chronic anticoagulation therapy decreases the incidence of thrombotic related events to between 1% to 4% per patient year. (Criscitiello, M. and Levine, H.: Thromboembolism and Prosthetic Heart Valves. Hospital Practice. Dec. 15, 1992:69–96.) Chronic anticoagulation therapy, however, carries with it a risk of hemorrhage similar in incidence to that of the residual risk for thrombotic events. (Barnhart, G. et al.: Degeneration and Calcification of Bioprosthetic Cardiac Valves. American Journal of Pathology. 1982, 106/1:136–139.)

Bioprosthetic valves initially approximate the hemodynamic properties of the natural valve. They carry a smaller risk of complications secondary to thrombus formation than do mechanical valves. Thus, chronic anticoagulation therapy need not be instituted in most patients. Bioprosthetic valves, however, carry a significantly higher risk of calcification than mechanical valves.

Calcification of bioprosthetic valves develops more rapidly in children, which have an incidence of calcification of about 40% to 50% at 4 years, than it develops in adults, which have an incidence of calcification of between 5% to 20% at 10 years. (Carpentier, A. et al.: Techniques for Prevention of Calcification of Valvular Bioprostheses. Circulation 70 (suppl I). 1984, I-165 to I-168.) Calcification causes thickening, retraction and reduced mobility of the leaflets and can lead to stenosis, insufficiency or both. Hence, calcification is an important limitation on the useful life expectancy of the currently used bioprosthetic valves. Since treatment of a functionally compromised bioprosthetic heart valve frequently requires replacement with a new valve, limitations on the useful life expectancy of a bioprosthetic heart valve are both a serious medical problem for the patient and a financial drain on the medical system.

Several methods to decrease or prevent bioprosthetic heart valve mineralization have been described in several patents since the problem was identified. Generally, the methods involve treating the bioprosthetic valve with various substances prior to implantation. Among the substances reported to work are sulfated aliphatic alcohols, phosphate esters, amino diphosphonates, derivatives of carboxylic acid and various surfactants. Nevertheless, none of these methods have proven completely successful in solving the problem of post-implantation mineralization. Thus, there remains a need for the bioprosthetic heart valve resistant to post-implantation mineralization.

SUMMARY OF THE INVENTION

In accordance with one aspect of the present invention, there is provided a controlled autolysis method for making a biological material substantially acellular, wherein the biological material that is to be made substantially acellular has structural integrity and comprises cells and non-cellular structural components, and wherein the controlled autolysis method comprises the step of exposing the biological material, prior to any fixation thereof, to at least one buffered solution having a pH in the range from about 5.0 to 8.0 and a temperature in the range from about 12° C. to 30° C. for a sufficient period of time to render at least one region of the biological material substantially acellular while substantially preserving the structural integrity and non-cellular structural components of the biological material.

In accordance with another aspect of the present invention, there is provided a bioprosthetic heart valve, comprising at least one leaflet that is adapted for reciprocal motion from an open position to a closed position upon blood flow through the valve, the at least one leaflet being formed, at least in part, of biological material that has been subjected to controlled autolysis, wherein the biological material that is subjected to controlled autolysis has structural integrity and comprises cells and non-cellular structural components.

In accordance with another aspect of the present invention, the bioprosthetic heart valve additionally comprises a generally tubular stent having an inflow end and an outflow end, wherein the at least one leaflet is positioned in relation to the stent such that the reciprocal motion of the at least one leaflet occurs as blood flows from the inflow end of the stent through the outflow end of the stent.

In accordance with another aspect of the present invention, there is provided a method of making a bioprosthetic heart valve, comprising the steps of (a) subjecting biological material to the controlled autolysis method of the present invention, wherein the biological material comprises a heart valve or a fragment of a heart valve, the heart valve or fragment of a heart valve comprising at least one leaflet, (b) fixing the biological material, and (c) fabricating the bioprosthetic heart valve from the biological material by the addition of non-biological material.

In accordance with another aspect of the present invention, there is provided a method of treating a mammal having a defective heart valve, comprising the steps of (a) providing a bioprosthetic heart valve, (b) removing the defective heart valve from the mammal, and (c) implanting the implanting the bioprosthetic heart valve in the mammal.

BRIEF DESCRIPTION OF THE FIGURES

The file of this patent contains at least one figure executed in color. Copies of this patent with color figures will be provided by the Patent and Trademark Office upon request and payment of the necessary fee.

DETAILED DESCRIPTION OF PREFERRED EMBODIMENTS

Figure 1:
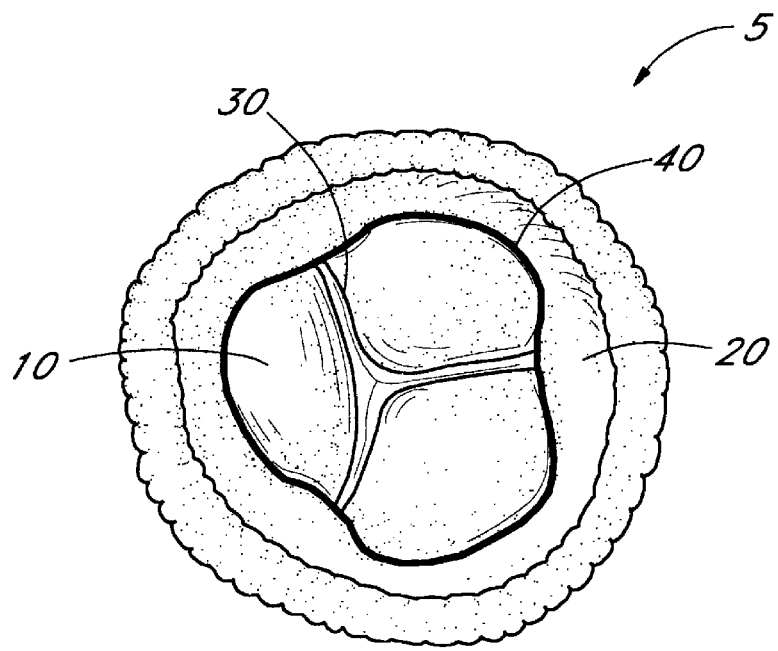
FIG. 1 is an outflow end elevational view of bioprosthetic heart valve.

In one aspect, the present invention relates to an improved bioprosthetic heart valve having an improved resistance to post-implantation mineralization. In this aspect, the invention involves the use of specially treated biological material. The material is treated by exposing the biological material, prior to fixation, to at least one buffered solution having a preselected pH range and a preselected temperature range for a sufficient period of time to render at least one region of the biological material substantially acellular while substantially preserving the non-cellular structural components of the biological material. This treatment involves the process hereinafter referred to as "controlled autolysis" and described more fully below.

Selected Definitions

As used herein, "biological material" comprises cells and non-cellular structural components derived from at least one of a living organism, a corpse, a carcass, an organ or part of an organ artificially maintained outside the living organism, a cell culture derived from a living organism, a corpse or a carcass, and a combination of the preceding. Biological material can be artificially manipulated prior to derivation from the above listed sources, such as by the introduction of special diets or drugs to the organism, or the introduction of gene sequences by an appropriate vector. Each biological material has a "structural integrity", as defined below.

As used herein, the terms "bovine", "porcine", "ovine" "Macropodidae" and "non-human primate" refer respectively to at least one animal of or related to a cow or ox, pig or hog, sheep or goat, a kangaroo, and monkey or ape or gibbon or chimpanzee or lemur. The terms include, but are not limited to, an unborn animal, young animal, male animal, female animal and pregnant animal, whether occurring naturally, through selective breeding or artificial insemination, a carcass, a fragment thereof, and a combination of any of the preceding. As used herein, "human" includes an embryo, a fetus, an unborn individual, a corpse, a fragment or tissue of any of the foregoing and a combination thereof.

As used herein, a "buffered solution" refers to an aqueous solution having at least one substance which tends to preserve hydrogen ion concentration or pH.

As used herein, "cell" means the composite of the membrane structures enveloping protoplasm and distinguishing the enveloped protoplasm from the external environment, wherein the membranes are identifiable by visual inspection with the aid of light microscopy. The cell can be living or not living. "Cell" also includes remnants or ghosts of the composite of the membrane structures indicating the former presence of a living cell at or near the location of the remnant or ghost.

As used herein, "membrane structures" refer to lipid layers and lipid bilayers, with or without proteins, carbohydrates, glycoproteins, cholesterol or other substances incorporated into the layers, such as are found enveloping protoplasm from a living cell.

As used herein, "non-cellular structural components" comprises substances not enveloped by the composite of the membrane structures of a cell, even if derived from or secreted by cells. The substances include collagen, elastin, laminin, teninsin, actinin and proteoglycans.

As used herein, "fixation" or "fixing" refers to a process of treating biological material so as to preserve the material from natural decay, including decay by autolysis. Fixation includes methods such as exposing the biological material to glutaraldehyde or formaldehyde.

As used herein, "fragment" means any portion or amount less than the whole, including disjoined or non-contiguous portions.

As used herein, "heart valve" means at least one of the aortic valve, mitral valve, tricuspid valve and pulmonary valves in a human, an equivalent valve in non-human animals, with or without intimately related tissue, a fragment thereof and a combination thereof.

As used herein, "region", as applied to biological material, refers to the whole biological material or any fragment of the biological material having macroscopically identified boundaries. For example, a region of a harvested natural heart valve can be the whole valve, at least one leaflet, the stent, the adjunct myocardium and a combination thereof.

As used herein, "structural integrity" refers to the natural capacity of biological material to perform a physical, as opposed to chemical, function in the organism, such as a compression function, a valvular function or a support function.

As used herein, "substantially acellular" and "substantial acellularity" interchangeably mean having at least about 70% (seventy percent) fewer cells than the natural or living state of the biological material. Therefore, biological material that has been made substantially acellular according to the present invention, has had the absolute number of cells reduced by at least about 70% from the natural state.

For the purposes of determining substantial acellularity, only cells native to the biological material are counted. Blood borne cells including red cells and platelets, as well as cells from other organisms are not counted.

The number of cells present in biological material is determined by using visual inspection of the material at about 20× (twenty times) to 100× (one hundred times) magnification using light microscopy with or without stain, or an equivalent technique. Satisfactory stains include standard stains known to those with skill in the art, as is appropriate to the specific cell type of the biological material being examined.

Conditions for Controlled Autolysis

Various aspects of the present invention utilize the process herein referred to as "controlled autolysis". "Controlled autolysis" means manipulating the physical conditions and storage solutions to which biological material is exposed to promote the breakdown of certain components of the biological material while substantially preserving other components due to properties of the autolytic enzymes found in the biological material. The treatment is performed prior to fixation.

Controlled autolysis can be used as a method of treating biological material that will be implanted into a human or animal to inhibit mineralization of regions of the biological material that are prone to mineralization after implantation. The treatment appears to inhibit mineralization by digesting cells, components of which attract minerals such as calcium after implantation, thereby allowing for the removal of the cells from the biological material. Controlled autolysis can also be used to render biological material substantially acellular for purposes other than inhibiting the post-implantation mineralization, such as for decreasing the immunogenicity or toxicity of the material.

Conditions important to produce controlled autolysis include pH, temperature, amount of solution per unit of biological material and time. In general, biological tissue to be processed by controlled autolysis is exposed to at least one buffered solution having a preselected pH range and a preselected temperature range for a sufficient period of time to complete the process.

The conditions for controlled autolysis are selected to advantageously promote activity of the autolytic enzymes which degrade cells while inhibiting, not affecting or promoting to a satisfactory minimal extent the autolytic enzymes that degrade non-cellular structural components. Further, these conditions advantageously maintain bacterial growth on the biological material to an acceptable level, preferably preventing log phase bacterial growth prior to completion of the treatment. By keeping the absolute bacteria burden on the biological tissue low, potential toxicity from bacterial components is reduced.

Controlled autolysis can be performed using any of a variety of buffered solutions known to those with skill in the art. Suitable buffered solutions include phosphate buffers, such as sodium phosphate monobasic and dibasic buffers, and phosphate citrate buffer. Any of a variety of other buffers well known by those of skill in the art can also be used. In one preferred embodiment, the buffered solution is sodium phosphate monobasic and dibasic buffers in saline solution at a pH of 7.4.

The aqueous portion of the buffered solution is preferably relatively pure. Water processed through a single distillation is satisfactory. Water processed by reverse osmosis filtration is also satisfactory. Double distilled water and water processed by both distillation and filtration is preferred but not necessary.

In one embodiment of the present invention, biological material is exposed to the buffered solution by immersion. As cells are degraded from the material, the degradation components are dispersed or solubilized in the buffered solution, thereby desirously leaching out of the material. It is therefore advantageous to keep the concentration of the cellular degradation components low in the buffered solution to promote this process.

Concentration of cellular degradation components can be kept low by regularly replacing the buffered solution. For example, biological material or groups of biological material can be positioned in containers of buffered solution. Racks carrying the biological materials can then be placed in different containers of fresh buffered solution as needed to keep the concentration of cellular degradation components in the buffered solution surrounding the biological material to a satisfactorily low level.

Alternately, biological material or groups of biological material can be positioned in containers of buffered solution and fresh buffered solution circulated in the container on a continuous or intermittent basis as needed. A combination of these methods, with or without equivalent methods, are contemplated within the scope of the present invention.

The preselected pH of the buffered solution can vary within a range from about 5.0 to about 8.0, more preferably 6.0 to 7.8. In one preferred embodiment, the preselected pH range is from about 7.2 to about 7.6. Using buffered solutions having a pH above about 7.8 to 8.0 disadvantageously promotes the activity of certain autolytic enzymes that degrade non-cellular structural components.

The preselected temperature range of the buffered solution can vary from about 12° C. to about 30° C., more preferably from about 15° C. to about 27° C. In one preferred embodiment, the preselected temperature range is from about 19° C. to about 23°C.

Temperatures significantly below about 12° C. decrease the activity of the autolytic enzymes which degrade cells, thereby disadvantageously prolonging the treatment time. Indeed, a temperature of about 5° C. can be used to preserve the biological tissue by suppressing the activity of the autolytic enzymes which degrade cells, among other enzymes. Temperatures above about 30° C. disadvantageously promote the autolytic enzymes that degrade non-cellular structural components, promote the denaturation of proteins present in the noncellular structural components and promote the growth of contaminating bacteria into the log phase before completion of the treatment. Temperatures between about 19° C. and 23° C. work particularly well because they allow the autolytic enzymes which degrade cells to function at a satisfactory rate, while suppressing bacterial growth to a satisfactory level.

The period of time sufficient to complete the process of controlled autolysis is judged by testing samples of the biological material to determine when at least one preselected region of the biological material has been rendered substantially acellular while substantially preserving the structural integrity and non-cellular structural components of the biological material. In general, the period of time can range from about a few hours to many days, depending on the preselected conditions of pH and temperature, type of biological material, quantity of biological material, degree of acellularity desired and other factors. The endpoint of the treatment can be determined by comparing the cellularity of treated biological tissue to a control or by counting the absolute number of cells in the preselected region and comparing the number to a known value for such a region.

In one preferred embodiment, the period of time is from about 24 hours to about 140 hours. In one particularly preferred embodiment, the period of time is from about 65 hours to about 75 hours. However, in certain circumstances period as short as 12 hours or shorter may be sufficient. Alternatively, other circumstances can require periods as long as 240 hours or longer.

A Bioprosthetic Heart Valve

Figure 2:
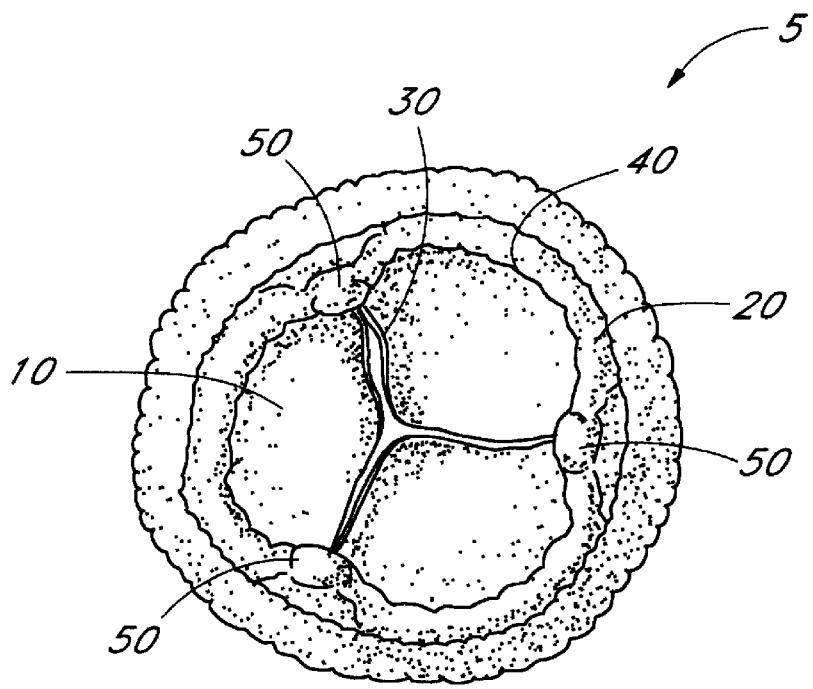
FIG. 2 is an inflow end elevational view of bioprosthetic heart valve.

Referring now to FIGS. 1 and 2 in detail, there is shown an outflow end elevational view and an inflow end elevational view, respectively, of a bioprosthetic heart valve 5 of the present invention. The valve has at least one leaflet that comprises a biological material. The biological material has at least one substantially acellular region, which can be produced in accordance with the controlled autolysis procedures described above.

The bioprosthetic heart valve 5 can comprise a stent 20, which can be formed from non-biological material in whole or in part. The non-biological material used to form the stent can be any of a variety of biocompatible materials well known to those with skill in the art.

The stent 20 is generally in the shape of a tube having a round or oval cross-sectional shape and an inner surface and an outer surface. The stent 20 can also have any of a number of projections such as 50, which can be used to attach the leaflets to the stent or to attach the valve to a vessel wall during implantation or for other reasons. The stent provides support for the at least one leaflet 10 and is adapted to permit blood flow therethrough.

The substantially acellular region of the biological material is preselected prior to treatment by the method of making biological tissue substantially acellular according to one aspect of the present invention. This region can be all of the biological material, the at least one leaflet, the stent, or a fragment or combination of all of the foregoing.

The at least one leaflet 10 has a base 40 which serves as an attachment point to the stent 20 and an edge 30. The at least one leaflet 10 is adapted for reciprocal motion from an open position to a closed position upon blood flow through the stent. In the closed position, the edge 30 serves as a point of coaptation with other leaflet edges, where present, or the stent, to inhibit retrograde flow of blood.

The biological material of the bioprosthetic heart valve can be derived from tissue of any of a variety of animals. Thus, tissues from a bovine, porcine, ovine, Macropodidae, nonhuman primate and human sources or a combination thereof can be used. In one preferred embodiment, the biological material is porcine in origin.

The biological material can be derived from a variety of tissues and organs including, but not limited to diaphragm, pericardium, heart valve, or a fragment or combination of all of the foregoing. In one preferred embodiment, the biological material is a heart valve, a fragment of a heart valve and a combination thereof.

Method of Making a Bioprosthetic Heart Valve

One of the aspects of the present invention relates to a method of making a bioprosthetic heart valve utilizing controlled autolysis. The method of making a bioprosthetic heart valve involves the provision of biological material as described above. The biological material has structural integrity and comprises both cells and non-cellular structural components. In one preferred embodiment, the biological material is derived from porcine heart valves.

The biological material is obtained from sources well known to those in the art. In one preferred embodiment, the biological material is derived from porcine heart valves obtained from a slaughterhouse which is subject to inspections specifically for the purpose of insuring the provision of suitable quality biological material. The biological material does not necessarily need to be harvested under sterile conditions, but it is preferred that such material be harvested under clean conditions to reduce the amount of contamination.

After harvesting, the biological material is immediately stored in a buffered solution having a temperature range from about 3°–10° C. An especially preferred pH range for this solution is from about 7.0 to about 7.8. Suitable buffers for storage are well known to those with skill in the art; these include any of a variety of phosphate and non-phosphate buffers. The temperature and pH of these buffers are selected so as to preserve the fresh state of the biological tissue until the biological tissue can be further processed by controlled autolysis. Thus, for certain buffers and conditions, the pH and temperature can be outside of these preferred ranges.

The biological tissue can be stored for an extended period of time, such as from days to weeks. However, most preferably, the biological tissue is further processed within hours of being harvested for maximum preservation of the structural components of the tissue. In a particularly preferred embodiment, the biological material begins the next step, a rinsing step, within 2–10 hours after harvesting.

When the biological tissue is ready for processing by controlled autolysis, it is first rinsed by placement in fresh buffered solution for several hours to a few days in order to reduce the amount of contaminants present on the biological material. In one preferred embodiment, the biological tissue is rinsed for approximately 24 hours.

The rinsing solution has the same temperature and pH ranges as the storage solution, such that the fresh state is still maintained while reducing the amount of contaminants. In a preferred embodiment, the temperature of the solution is about 3°–7° C. and the pH is from about 7.2–7.6. Buffer solutions suitable for rinsing are the same as those suitable for storing the freshly harvested biological material, and are well known to those with skill in the art.

The amount of rinsing solution varies with the amount of biological tissue to be rinsed. When the biological material is porcine heart valves, approximately 100–300 ml of rinsing solution is adequate. In one preferred embodiment where the biological material is porcine heart valves, approximately 100 ml of rinsing solution per valve is used.

Controlled autolysis is initiated by transferring the biological material to a container of fresh buffered solution or replacing the rinsing solution with fresh buffered solution. This constitutes the first treatment stage of controlled autolysis. The amount of buffered solution again varies with the amount of biological material but should be enough to cover the material completely and allow for dilution of the extracted cells during the process. When the biological material is porcine heart valves, approximately 100–300 ml of buffered solution is adequate. In one preferred embodiment where the biological material is porcine heart valves, approximately 200 ml of solution per valve is used. Thus, where approximately 40 porcine heart valves are to be processed by controlled autolysis in one container, approximately 8000 ml total of buffered solution will be present in the container.

The buffered solution can be an aqueous solution of any of a variety of buffers. Suitable buffered solutions include phosphate buffers, such as sodium phosphate monobasic and dibasic buffers, and phosphate citrate buffer. Any of a variety of other buffers well known by those of skill in the art can also be used. In one preferred embodiment, the buffered solution is sodium phosphate monobasic and dibasic buffers in saline solution.

The buffered solution should maintain the biological tissue at a pH of between 6.0 and 8.0. In a preferred embodiment the pH is between 7.0 and 7.8. When the biological tissue is porcine heart valves, it is preferred that the pH be between 7.2 and 7.6.

The temperature of the buffered solution can vary from about 12° C. to about 30° C., more preferably from about 15° C. to about 27° C. In one preferred embodiment, the temperature range of the buffered solution is from about 19° C. to about 23° C.

Temperatures significantly below about 12° C. decrease the activity of the autolytic enzymes which degrade cells. Temperatures above about 30° C. disadvantageously promote the autolytic enzymes that degrade non-cellular structural components, promote the denaturation of proteins present in the non-cellular structural components and promote the growth of contaminating bacteria into the log phase before completion of the treatment. Temperatures between about 19° C. and 23° C. work particularly well because they allow the autolytic enzymes which degrade cells to function at a satisfactory rate, while suppressing bacterial growth to a satisfactory level.

Where the biological tissue is porcine heart valves, the valves are arranged in the container in a single layer and covered by the buffered solution. Gentle agitation is used to promote removal of the cells from the valves.

The biological tissue is maintained in the container for a period of time ranging from hours to days. In a preferred embodiment, the biological material is maintained in the container for approximately 24 hours.

Next, the valves are rinsed in fresh buffered saline having the same or an equivalent buffer as is used in the first treatment stage of controlled autolysis and transferred to another container having buffered solution with parameters similar to the first treatment stage of controlled autolysis. Essentially, the first stage of controlled autolysis is then repeated, constituting a second stage of controlled autolysis.

After completion of the second stage of controlled autolysis, additional stages may be performed if necessary to achieve the desired level of acellularity. In a preferred embodiment, three stages are performed totaling a period of approximately 72 hours total for treatment by controlled autolysis.

After completion of controlled autolysis, or during the process, a sample or samples of the biological material are checked for the level of acellularity by methods well known to those with skill in the art and varying by the type of biological tissue being treated. For example, microscopic examination using cryosectioning or paraffin sectioning techniques or other techniques may be used.

Once the treatment is completed, the biological material is processed and fabricated into finished bioprosthetic heart valves using standard techniques well known to those with skill in the art. This may include fixation, such as by glutaraldehyde, sterilization with radiation or chemicals, and the addition of non-biological material to the biological material, such as by the addition of a stent, all processes well known to those with skill in the art. An example of a finished bioprosthetic valve made according to this method is found in the section titled "A Bioprosthetic Heart Valve", above.

Method of treating a human or animal with a defective heart valve

In another aspect, the present invention is a method of treating a mammal with a defective heart valve. The method of treating involves the provision of a heart valve made according to the method of described in the section titled "Method of Making a Bioprosthetic Heart Valve." The defective heart valve is removed and the bioprosthetic heart valve implanted in the mammal.

Method of Treating Biological Material For Incorporation Into a Bioprosthetic Heart Valve In another aspect, the present invention is a method of utilizing controlled autolysis to treat biological material that is incorporated into a bioprosthetic heart valve, or that will be incorporated into a bioprosthetic heart valve, to inhibit post-implantation mineralization of the bioprosthetic heart valve. The method of treating the biological material involves providing biological material, as described above. The biological material has structural integrity and comprises both cells and non-cellular structural components. The biological material is exposed, prior to fixation, to at least one buffered solution having a preselected pH range and a preselected temperature range for a sufficient period of time to render at least one preselected region of the biological material substantially acellular while substantially preserving the structural integrity and non-cellular structural components of the biological material as is described more fully above. In addition to these steps, the biological material can be further processed or altered, as also described in the sections above.

Method of Making Biological Material Substantially Acellular

In a further aspect, the present invention is a method of utilizing controlled autolysis to make biological material substantially acellular. The method involves providing biological material. The biological material has structural integrity and comprises both cells and non-cellular structural components. The biological material is exposed, prior to fixation, to at least one buffered solution having a preselected pH range and a preselected temperature range for a sufficient period of time to render at least one preselected region of the biological material substantially acellular while substantially preserving the structural integrity and non-cellular structural components of the biological material.

The biological material suitable for treatment by this method can be derived from any of a variety of animal tissue. Thus, tissues from a bovine, porcine, ovine, Macropodidae, nonhuman primate and human sources or a combination thereof can be used. In one preferred embodiment, the biological material is porcine in origin.

The biological material can be derived from a variety of tissues and organs including, but not limited to diaphragm, pericardium, heart valve, umbilical cord, artery, vein, facia lata, dura mater, tendon, ligament, tympanic membrane, or a fragment or combination of all of the foregoing. In one preferred embodiment, the biological material is a heart valve, a fragment of a heart valve and a combination of the foregoing.

Figure 3:
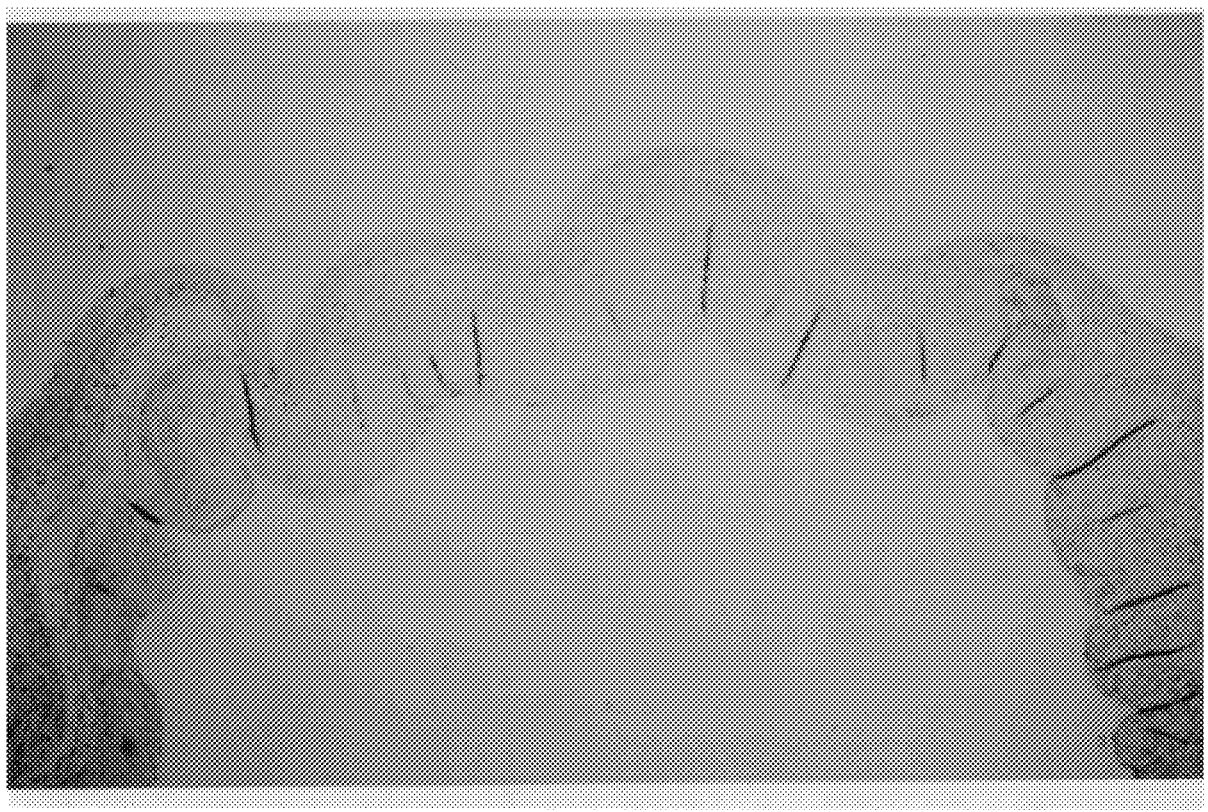
FIG. 3 is a photomicrograph of a cross-section of a porcine aortic valve leaflet before treatment at 20× (twenty times magnification).

Referring now to FIG. 3, there is provided a photomicrograph of a cross-section of a porcine aortic valve leaflet, which is biological material suitable for use in the method of making a bioprosthetic heart valve in accordance with one aspect of the present invention. The biological material was stained with hematoxylin and eosin using standard techniques and the photomicrograph taken under low power, 20× (twenty times magnification). The cell nuclei present in the tissue are represented by the small dark purple spots visible throughout most areas of the tissue.

Figure 4:
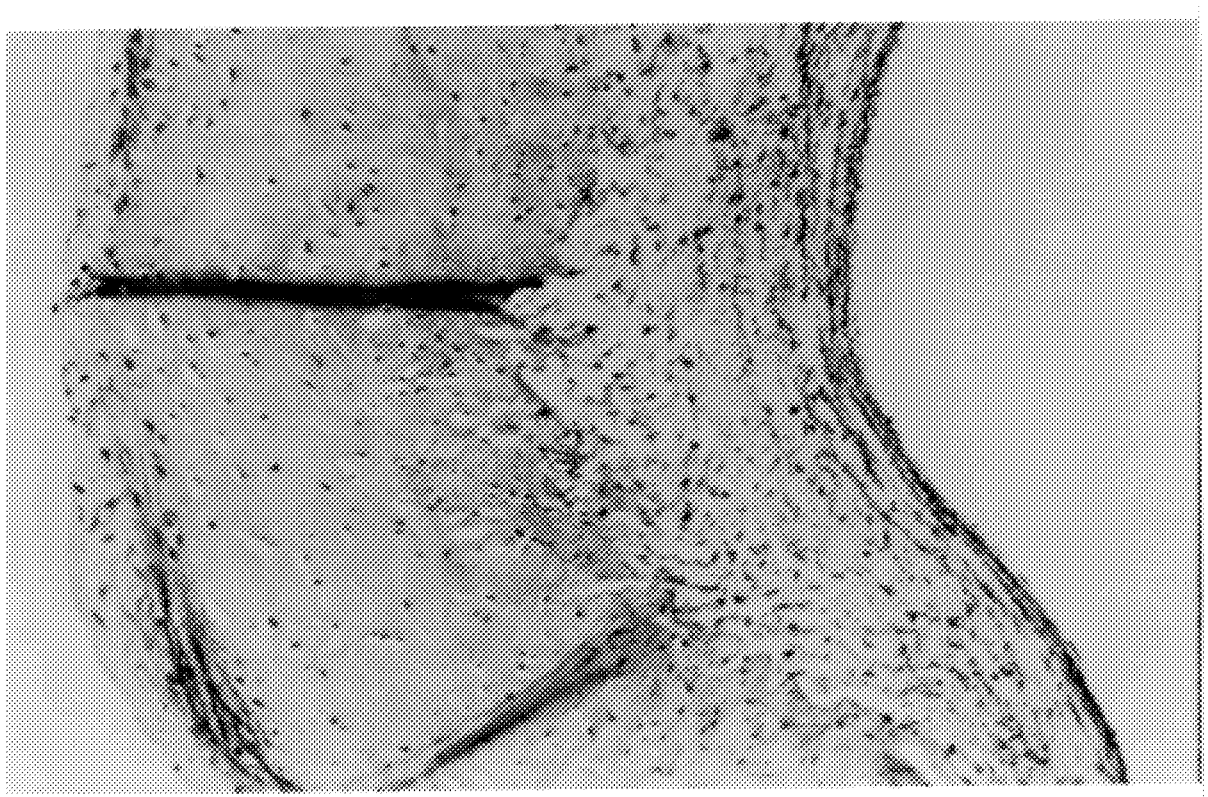
FIG. 4 is a photomicrograph of a cross-section of a porcine aortic valve leaflet before treatment at 100× (one hundred times magnification).

Referring now to FIG. 4, there is provided a photomicrograph of a cross-section of a porcine aortic valve leaflet, similar to the porcine aortic valve leaflet shown in FIG. 3, but taken under 100× (one hundred times magnification). The cell nuclei present in the biological tissue are again represented by the small dark purple spots visible throughout most areas of the tissue. The tissue shown in both FIG. 3 and FIG. 4 had not been subject to the process of controlled autolysis as described herein.

Figure 5:
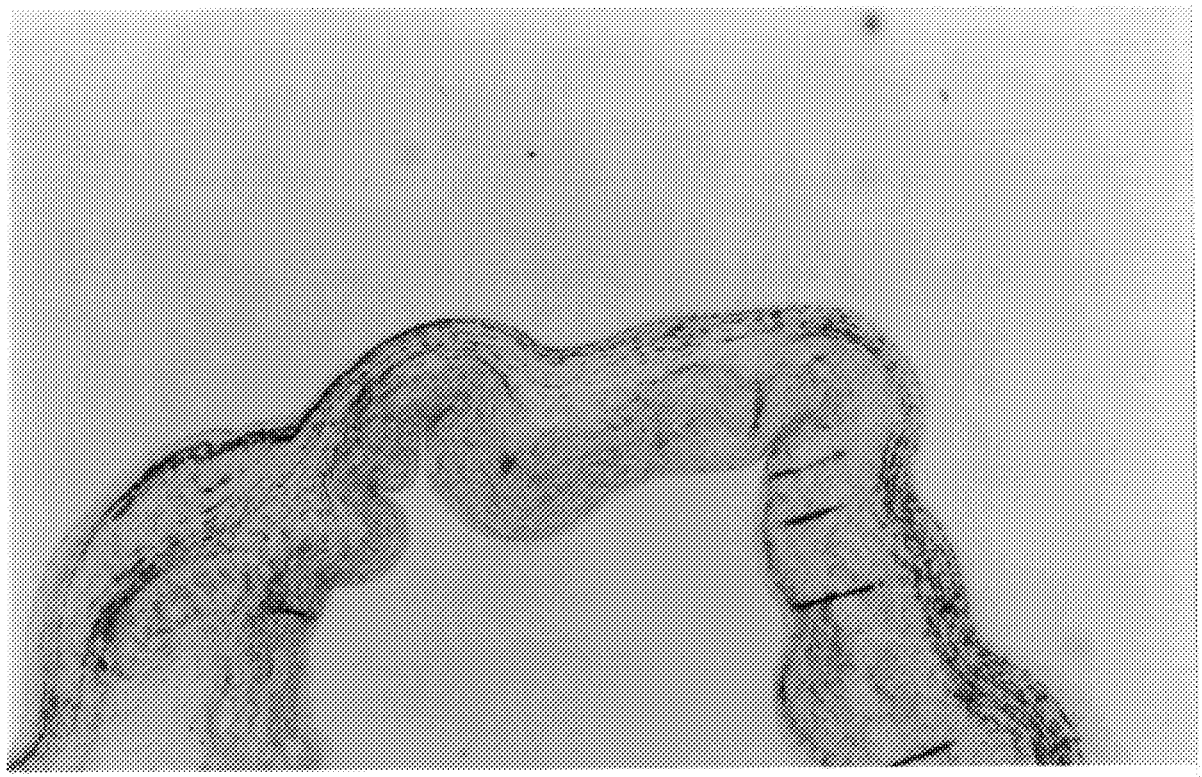
FIG. 5 is a photomicrograph of a cross-section of a porcine aortic valve leaflet after treatment at 20× (twenty times magnification).
Figure 6:
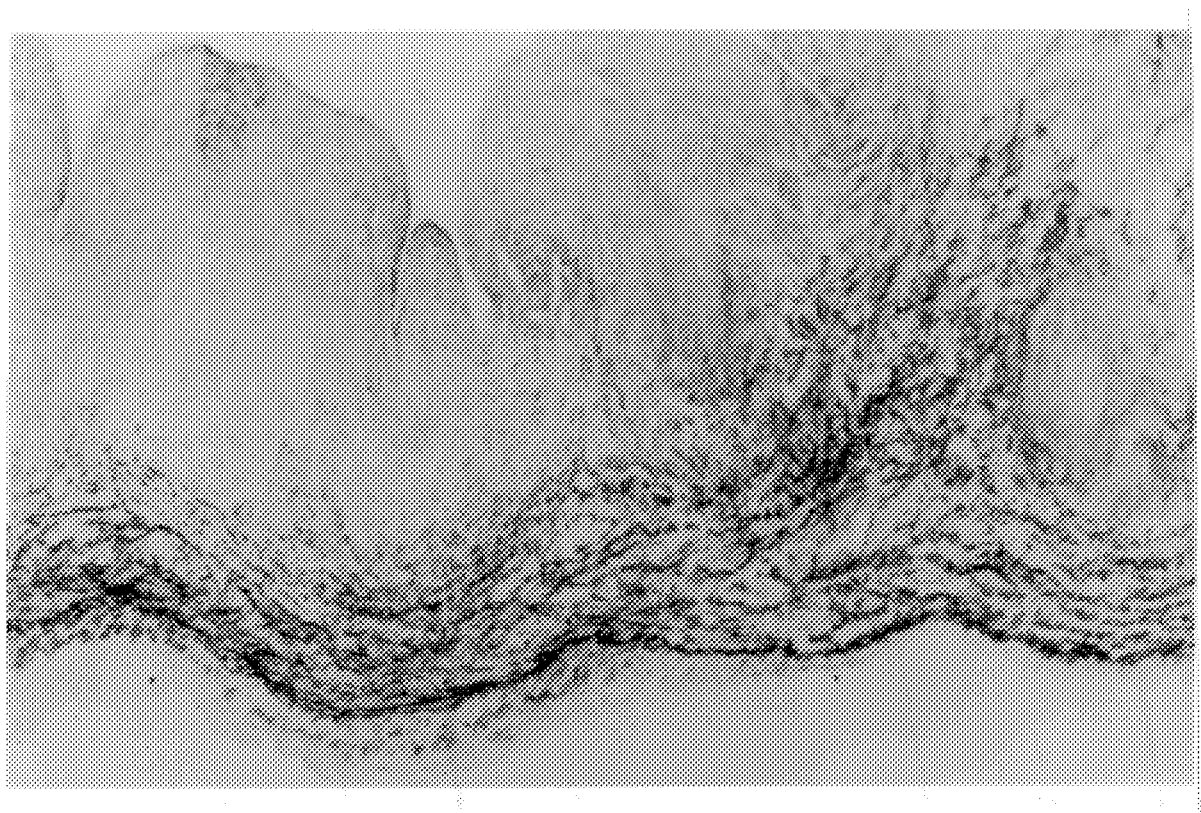
FIG. 6 is a photomicrograph of a cross-section of a porcine aortic valve leaflet after treatment at 40× (forty times magnification).

Referring now to FIGS. 5 and 6, there are provided photomicrographs of a cross-section of a porcine aortic valve leaflet, similar to FIGS. 3 and 4, but taken after the biological tissue has been subject to the process of controlled autolysis as described herein in the method of making biological tissue acellular.

FIG. 5 was taken under low power, 20× (twenty times magnification) and FIG. 6 was taken under 40× (forty times magnification). The biological tissue was stained by standard techniques such that collagen appears pink to red and elastin appears black.

Note that in both FIGS. 5 and 6, there appears to be a near complete absence of cells nuclei indicating that the tissue has been rendered substantially acellular by the controlled autolysis treatment. Further, note that the non-cellular structural components of the biological material, here collagen and elastin, appear to have been substantially preserved and that the structural architecture of the leaflet is substantially intact.

Method of Treating Biological Material To Inhibit Post-Implantation Mineralization In one aspect, the present invention is a method of utilizing controlled autolysis to treat biological material that will be implanted into a human or animal to inhibit mineralization of regions of the biological material that are prone to mineralization after implantation into the human or animal. The method comprises providing biological material as described above and treating the biological material as described in the section titled "Method of Making Biological Material Substantially Acellular".

Figure 7:
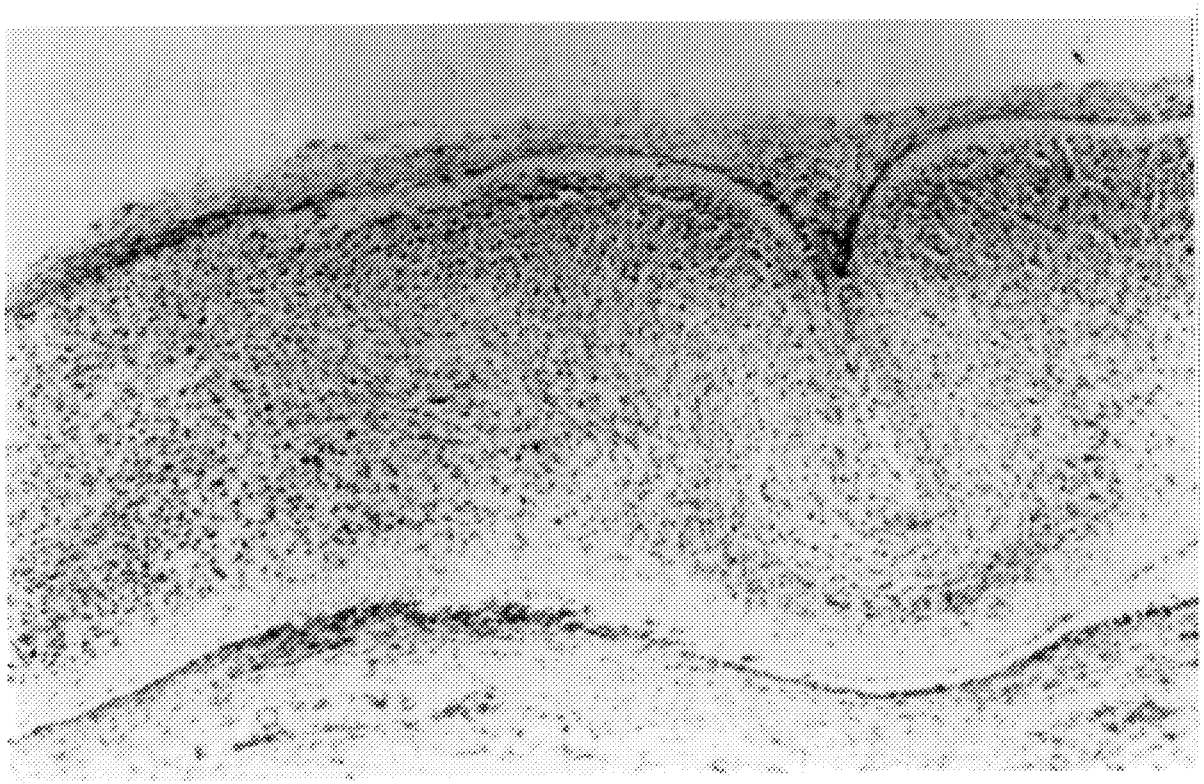
FIG. 7 is a photomicrograph of a cross-section of a porcine aortic valve leaflet 2 (two) weeks after implantation that had not been treated at 40× (forty times magnification).

Referring now to FIG. 7, there is provided a photomicrograph of a cross-section of a porcine aortic valve leaflet, taken under 40× (forty times magnification). The biological tissue did not undergo treatment by controlled autolysis, as described herein, but instead was processed by standard techniques. The leaflet was placed in a subcutaneous pocket in the dorsum of a juvenile rat for two weeks. Upon removal, it was sectioned and stained by the method of Von Kossa, which visualizes mineralized material by depositing reduced silver in association with phosphate salts, in this case presumably calcium phosphate. The tissue was counterstained with hematoxylin and eosin. Note that Von Kossa positive material is present throughout the biological material, indicating considerable mineralization of the biological material.

Figure 8:
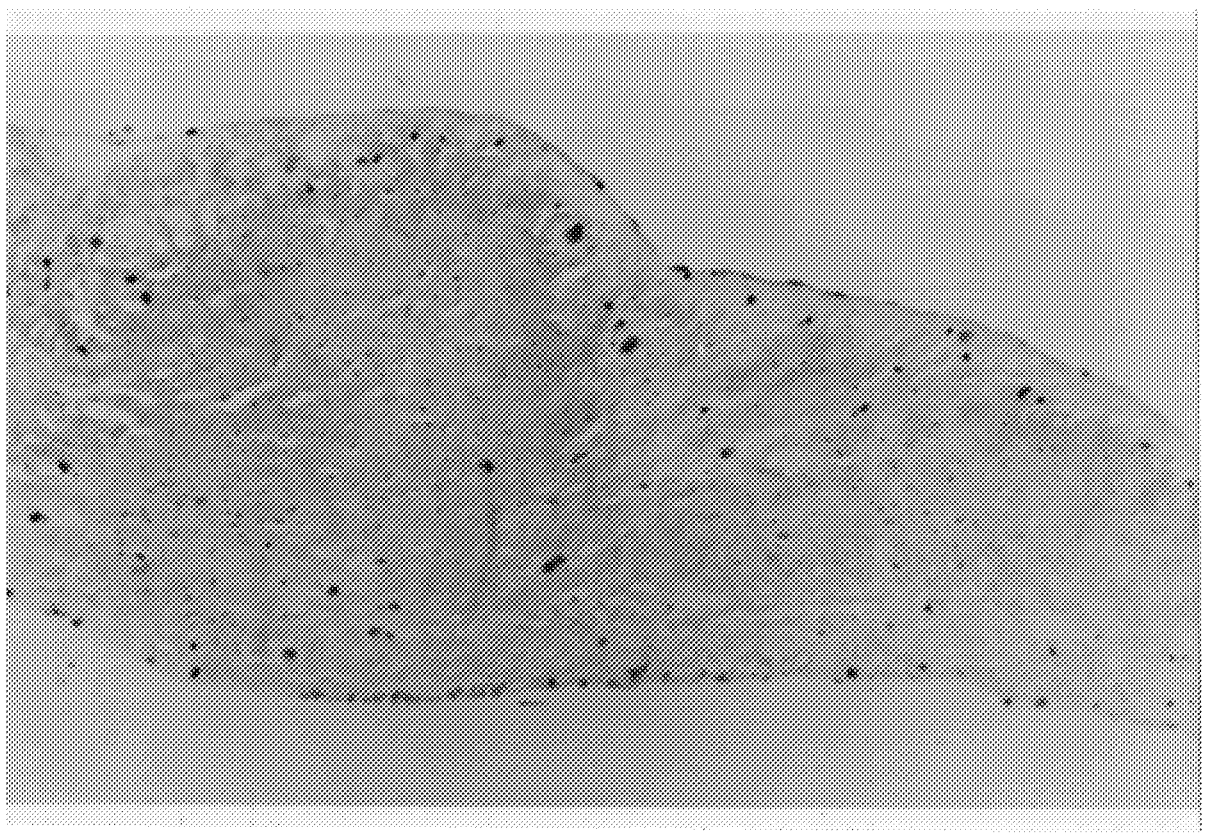
FIG. 8 is a photomicrograph of a cross-section of a porcine aortic valve leaflet 20 (twenty) weeks after implantation that had been treated at 40× (forty times magnification).

Referring now to FIG. 8, there is provided a photomicrograph of a cross-section of a porcine aortic valve leaflet, taken under 40× (forty times magnification). The biological tissue was processed by controlled autolysis, as described herein. The leaflet was used in the fabrication of a complete valve and implanted in a sheep in the mitral position for a period of 20 (twenty) weeks. Upon removal, it was sectioned and stained by the method of Von Kossa and counterstained with hematoxylin and eosin.

The dark purple spots in FIG. 8 represent cell nuclei of host cells that have attached to the surface of the leaflet and that have migrated into the leaflet. The small black spots represent normal background staining associated with the Von Kossa technique. Note that this section shows no evidence of intrinsic leaflet mineralization.

EXAMPLE:
Making a Bioprosthetic Heart Valve

A bioprosthetic heart valve was made according to the method described above. Forty fresh porcine aortic valves were obtained from the slaughterhouse. The valves were harvested under clean, but not sterile, conditions using techniques well known in the art. The valves were immediately stored in a solution of phosphate buffered saline at a temperature of 5°–10° C. to preserve the fresh state.

Approximately 4 hours after harvesting, the valves were rinsed by placing them in a phosphate buffered saline solution of approximately 100 ml per valve and having a pH of approximately 7.4 for approximately 24 hours at 3°–7° C. to reduce the amount of contaminants present on the valves.

The valves were then transferred to a container having approximately 200 ml of phosphate buffered saline solution per valve for a total of approximately 8000 ml, at a pH of 7.4 and a temperature of 21°±2° C. The valves were arranged in the container in a single layer and covered by the buffered solution. Gentle agitation was initiated to promote removal of the cells from the valves. The valves were maintained in the container for approximately 24 hours.

Next, the valves were rinsed in fresh buffered saline and transferred to another container having approximately 200 ml of fresh phosphate buffered saline per valve, for a total of approximately 8000 ml, at a pH of 7.4 and a temperature of 21°±2° C. Once again, gentle agitation was used and the valves remained in the container for approximately 24 hours.

Next, the valves were again rinsed in fresh buffered saline and transferred to another container having approximately 200 ml of fresh phosphate buffered saline per valve, for a total of approximately 8000 ml, at a pH of 7.4 and a temperature of 21°±2° C. As before, gentle agitation was used.

After an additional 24 hours, a random sample of four valves was selected for microscopic examination using paraffin sectioning techniques well known to those with skill in the art. Regions of the leaflets were examined and found to contain less than 2 (two) cells per 400× (four hundred times) field. This number of cells is indicative of a greater than 90% loss of cells for porcine heart valves. The treatment was, therefore, considered complete and the valves were then fixed, processed and fabricated into finished bioprosthetic heart valves using standard techniques well known to those with skill in the art.

After processing and final fabrication, the bioprosthetic heart valves were tested by an extended accelerated fatigue test, according to standard techniques for the industry. Adequate performance at a level of 200 million cycles indicates that the valve tested retains the necessary structural integrity. The valves made according to the present invention were found to perform adequately for greater than 200 million cycles. Using this technique, greater than 75% of the batches are made satisfactorily acellular by approximately 72 hours, while maintaining necessary structural integrity.

Although this invention has been described in terms of certain preferred embodiments, other embodiments that are apparent to those of ordinary skill of art are also within the scope of the invention. Accordingly, the scope of the invention is intended to be defined only by reference to the appended claims.

We claim:

1. A method of making a bioprosthetic heart valve comprising the steps of:

exposing biological material comprising cellular and non-cellular structural components to at least one buffered solution having a pH in the range from about 5.0 to about 8.0 and a temperature in the range from about 12° C. to about 30° C. for a sufficient period of time to facilitate the degradation of said cells by autolytic enzymes within said cells, whereby at least one region of biological material is rendered substantially acellular while preserving the overall structural integrity and non-cellular structural components of the biological material, wherein the exposure occurs prior to any fixation of the biological material;

fixing the biological material; and fabricating the bioprosthetic heart valve from the biological material by the addition of non-biological material.

2. The method of claim 1, wherein the biological material is derived from at least one animal selected from the group consisting of a bovine, a porcine, an ovine, a Macropodidae, a nonhuman primate, a human and a combination of any of the foregoing.

3. The method of claim 1, wherein the biological material is derived from a porcine.

4. The method of claim 1, wherein the biological material is at least one material selected from the group consisting of diaphragm, pericardium, heart valve, umbilical cord, artery, vein, fascia lata, dura mater, tendon, ligament, tympanic membrane, a fragment of any of the foregoing and a combination of any of the foregoing.

5. The method of claim 1, wherein the biological material is at least one material selected from the group consisting of a heart valve, a fragment of a heart valve and a combination of the foregoing.

6. The method of claim 1, wherein the biological material is a leaflet of a heart valve.

7. The method of claim 1, wherein the noncellular structural components include at least one structural component selected from the group consisting of collagen, elastin, laminin, teninsin, actinin, proteoglycans, a fragment of any of the foregoing and a combination of any of the foregoing.

8. The method of claim 1, wherein the buffered solution is at least one solution selected from the group consisting of sodium phosphate monobasic buffer, sodium phosphate dibasic buffers, phosphate citrate buffer and a combination of any of the foregoing.

9. The method of claim 8, wherein the buffered solution is a combination of sodium phosphate monobasic and dibasic buffers.

10. The method of claim 1, wherein the pH range is from about 6.0 to about 8.0.

11. The method of claim 10, wherein the pH range is from about 7.2 to about 7.6.

12. The method of claim 1, wherein the temperature range is from about 19° C. to about 23° C.

13. The method of claim 1, wherein the period of time is from about 24 hours to about 100 hours.

14. The method of claim 1, wherein the period of time is from about 65 hours to about 75 hours.

15. The method of claim 1, wherein the bioprosthetic heart valve comprises at least one leaflet formed, at least in part, of the biological material, wherein the at least one leaflet is adapted for reciprocal motion from an open position to a closed position upon blood flow through the valve.

16. The method of claim 15, wherein the bioprosthetic heart valve additionally comprises a generally tubular stent having an inflow end and an outflow end, and wherein the at least one leaflet is positioned in relation to the stent such that the reciprocal motion of the at least one leaflet occurs as blood flows from the inflow end of the stent through the outflow end of the stent.

17. The method of claim 16 wherein the stent has a generally circular cross-section.

18. The method of claim 16, wherein the stent has an inner surface and an outer surface and wherein the at least one leaflet is attached to the inner surface.

19. The method of claim 16, wherein the stent comprises non-biological material.

20. The method of claim 16 wherein the stent is adapted to permit blood flow therethrough.

21. The method of claim 15, wherein the at least one region of the biological material that is rendered substantially acellular is substantially all of the leaflet.

22. A method of making a bioprosthetic heart valve comprising the steps of:

performing controlled autolysis on biological material comprising cellular and non-cellular structural components, said controlled autolysis consisting essentially of exposing said biological material to at least one solution consisting essentially of a buffer having a pH in the range from about 5.0 to about 8.0 and a temperature in the range from about 12° C. to about 30° C. for a sufficient period of time to facilitate the degradation of said cells by autolytic enzymes within said cells whereby at least one region of the biological material is rendered substantially acellular while preserving the overall structural integrity and non-cellular structural components of the biological material, wherein the exposure occurs prior to any fixation of the biological material; and fabricating the bioprosthetic heart valve from the biological material by the addition of non-biological material.

23. The method of claim 22 further comprising fixing said biological material.

24. The method of claim 22, wherein the biological material is derived from at least one animal selected from the group consisting of a bovine, a porcine, an ovine, a Macropodidae, a nonhuman primate, a human and a combination of any of the foregoing.

25. The method of claim 22, wherein the biological material is at least one material selected from the group consisting of diaphragm, pericardium, heart valve, umbilical cord, artery, vein, fascia lata, dura mater, tendon, ligament, tympanic membrane, a fragment of any of the foregoing and a combination of any of the foregoing.

26. The method of claim 22, wherein the noncellular structural components include at least one structural component selected from the group consisting of collagen, elastin, laminin, teninsin, actinin, proteoglycans, a fragment of any of the foregoing and a combination of any of the foregoing.

27. The method of claim 22, wherein the buffered solution is at least one solution selected from the group consisting of sodium phosphate monobasic buffer, sodium phosphate dibasic buffers, phosphate citrate buffer and a combination of any of the foregoing.

28. The method of claim 22, wherein the bioprosthetic heart valve comprises at least one leaflet formed, at least in part, of the biological material, wherein the at least one leaflet is adapted for reciprocal motion from an open position to a closed position upon blood flow through the valve.

29. The method of claim 28, wherein the bioprosthetic heart valve additionally comprises a generally tubular stent having an inflow end and an outflow end, and wherein the at least one leaflet is positioned in relation to the stent such that the reciprocal motion of the at least one leaflet occurs as blood flows from the inflow end of the stent through the outflow end of the stent.

30. The method of claim 29, wherein the stent has an inner surface and an outer surface and wherein the at least one leaflet is attached to the inner surface.

31. The method of claim 29, wherein the stent comprises non-biological material.

32. The method of claim 28, wherein the at least one region of the biological material that is rendered substantially acellular is substantially all of the leaflet.

* * * * *